US012718925B2

(12) United States Patent
Wabel et al.

(10) Patent No.: US 12,718,925 B2
(45) Date of Patent: Aug. 25, 2026

(54) DIALYSIS TREATMENT MODALITIES; METHOD AND DEVICES

(71) Applicant: Fresenius Medical Care Deutschland GmbH, Bad Homburg (DE)

(72) Inventors: Peter Wabel, Rosbach (DE); Ulrich Moissl, Karben (DE); Paul Chamney, Tring (GB)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 360 days.

(21) Appl. No.: 17/311,586

(22) PCT Filed: Dec. 18, 2019

(86) PCT No.: PCT/EP2019/086022
§ 371 (c)(1),
(2) Date: Jun. 7, 2021

(87) PCT Pub. No.: WO2020/127535
PCT Pub. Date: Jun. 25, 2020

(65) Prior Publication Data

US 2022/0028523 A1 Jan. 27, 2022

(30) Foreign Application Priority Data

Dec. 19, 2018 (EP) .................................... 18214099

(51) Int. Cl.
*G16H 20/40* (2018.01)
*A61M 1/14* (2006.01)
(Continued)

(52) U.S. Cl.
CPC ............ *G16H 20/40* (2018.01); *A61M 1/159* (2022.05); *A61M 1/282* (2014.02);
(Continued)

(58) Field of Classification Search
CPC ........ G16H 20/40; G16H 10/60; G16H 40/40; G16H 50/20; G16H 50/30
See application file for complete search history.

(56) References Cited

U.S. PATENT DOCUMENTS 8,692,167 B2 4/2014 Hedmann et al.
9,555,181 B2 1/2017 Hedmann et al.
(Continued)

FOREIGN PATENT DOCUMENTS

EP 1763316 8/2011
EP 2578147 4/2013
(Continued)

OTHER PUBLICATIONS

Fresenius Medical Care, "Peritonealdialyse PatientOnLine Der PD-Therapie-Manager," Jun. 7, 2011, retrieved Sep. 1, 2021, retrieved from URL <https://www.freseniusmedicalcare.com/fileadmin/data/de/pdf/Healthcare_Professionals/PD/Broschuere_PatientOnline.pdf>, 24 pages (with machine translation) (Year: 2011).*
(Continued)

*Primary Examiner* — Robert A Sorey
*Assistant Examiner* — Kristine K Rapillo
(74) *Attorney, Agent, or Firm* — Fish & Richardson P.C.

(57) ABSTRACT

The present disclosure relates to methods for determining at least one treatment modality of a dialysis treatment of a specific patient depending on at least one value out of the group of values, a first value reflecting the overhydration (OH) of the patient, a second value reflecting the salinity or osmolarity of the patient, a third value reflecting the blood pressure of the patient, a fourth value reflecting the renal function of the patient, a fifth value reflecting a heart issue the patient, a sixth value reflecting hypotension of the patient, a seventh value reflecting vessel conditions, and an eighth value reflecting a total protein content of the patient.
(Continued)

Herein, an algorithm or reference material is used. Furthermore, the disclosure relates to devices for executing this method and processing the results of the method.

23 Claims, 13 Drawing Sheets

(51) Int. Cl.

| | |
|---|---|
| ***A61M 1/28*** | (2006.01) |
| ***A61M 1/34*** | (2006.01) |
| ***G16H 10/60*** | (2018.01) |
| ***G16H 40/40*** | (2018.01) |
| ***G16H 40/67*** | (2018.01) |
| ***G16H 50/20*** | (2018.01) |
| ***G16H 50/30*** | (2018.01) |
| ***G16H 50/70*** | (2018.01) |
| ***G16H 70/20*** | (2018.01) |
| ***G16H 70/40*** | (2018.01) |
| *G01N 33/48* | (2006.01) |

(52) U.S. Cl.

CPC .......... *A61M 1/3403* (2014.02); *G16H 10/60* (2018.01); *G16H 40/40* (2018.01); *G16H 40/67* (2018.01); *G16H 50/20* (2018.01); *G16H 50/30* (2018.01); *G16H 50/70* (2018.01); *G16H 70/20* (2018.01); *G16H 70/40* (2018.01); *A61M 1/152* (2022.05); *A61M 2205/18* (2013.01); *A61M 2205/3303* (2013.01); *G01N 33/48* (2013.01)

(56) References Cited

U.S. PATENT DOCUMENTS

| | | | | |
|---|---|---|---|---|
| 2007/0112297 A1 | 5/2007 | Plahey et al. | | |
| 2012/0168426 A1 | 7/2012 | Hedmann et al. | | |
| 2014/0088442 A1* | 3/2014 | Soykan | A61B 5/0205 | 600/483 |
| 2015/0034536 A1* | 2/2015 | Rada | A61M 1/342 | 210/85 |
| 2018/0236157 A1 | 8/2018 | Wolf et al. | | |
| 2019/0134290 A1* | 5/2019 | Pouchoulin | A61M 1/1609 | |

FOREIGN PATENT DOCUMENTS

| | | |
|---|---|---|
| WO | 2006/002685 | 1/2006 |
| WO | 2012/076179 | 6/2012 |
| WO | 2016/151087 | 9/2016 |
| WO | 2017/025200 | 2/2017 |

OTHER PUBLICATIONS

Amici, G. (2013). Prescription in peritoneal dialysis. Journal of Nephrology, 26(21), 83-95. https://doi.org/10.5301/JN.2013.11635 (Year: 2013).*

Fresenius Medical Care, "Peritonealdialyse PatientOnLine Der PD-Therapie-Manager," Jun. 7, 2011, retrieved Sep. 1, 2021, retrieved from URL (https://www.freseniusmedicalcare.com/fileadmin/data/de/pdf/Healthcare_Professionals) PD/Broschuere_PatientOnline.pdf>, 24 pages (with machine translation). (Year: 2021).*

Van den Berg, R., Cnossen, T. T., Konings, C. J. A. M., Kooman, J. P., van der Sande, F. M., & Leunissen, K. M. L. (2008). Different treatment options in peritoneal dialysis. Nephrology Dialysis Transplantation, 1(4), iv14-iv17. https://doi.org/10.1093/ndtplus/sfn1 18 (Year: 2008).*

Amici et al., "Prescription in peritoneal dialysis," Journal of Nephrology, Nov. 2013, 26(Suppl 21):S83-S95.

Fresenius Medical Care, "2008K Hemodialysis Machine Operator's Manual," Apr. 28, 2016, retrieved on September 1. 2021, retrieved from URL <https://data2.manualslib.com/pdf2/44/4396/439583-fresenius_medical_care/2008k.pdf?063734fb1255f2f70a25010fa5185dfd>, 208 pages.

Fresenius Medical Care, "Peritonealdialyse PatientOnLine Der PD-Therapie-Manager," Jun. 7, 2011, retrieved Sep. 1, 2021, retrieved from URL <https://www.freseniusmedicalcare.com/fileadmin/data/de/pdf/Healthcare_Professionals/PD/Broschuere_PatientOnline.pdf>, 24 pages (with machine translation).

International Search Report and Written Opinion in International Appln. No. PCT/EP2019/086022, mailed Feb. 19, 2020, 14 pages.

Trinh et al., "The Dialysis Sodium Gradient: A Modifiable Risk Factor for Fluid Overload," Nephron Extra, Feb. 2017, 7(1):10-17.

* cited by examiner

DIALYSIS TREATMENT MODALITIES; METHOD AND DEVICES

CROSS-REFERENCE TO RELATED APPLICATIONS

The present application is the national stage entry of International Patent Application No. PCT/EP2019/086022, filed on Dec. 18, 2019, and claims priority to application Ser. No. 18/214,099.6, filed in Europe on Dec. 19, 2018, the disclosures of which are expressly incorporated herein in their entireties by reference thereto.

TECHNICAL FIELD

The present disclosure relates to methods for determining at least one treatment modality of a dialysis treatment of a specific patient. Furthermore, the disclosure relates to devices for executing this method and possibly to process the results of the method. The devices may in turn be comprised of or be connected to a treatment apparatus. The disclosure relates further to a treatment modality. Moreover, a digital storage unit, a computer program product and a computer program are specified.

BACKGROUND

In clinical settings, patients who suffer from renal dysfunction are treated using dialysis apparatuses. The modalities of the particular treatment sessions, which may include fluid flows to be set or achieved, pressure thresholds to be monitored and complied with, maximum durations to be observed, fluid volumes to be conveyed, such as an ultrafiltration volume or drugs used and their particular dosage or concentration, can be set in advance of the treatment session. They can be set using an interface of the apparatus, they can be suggested or prescribed by the doctor, and the like. Any setting may, under certain circumstances, contribute to the patient's benefit but have its downsides under other circumstances. Hence, there is a huge demand for different treatment regimens. Also, there is a need for methods for setting certain modalities (e.g., configurations) of the patient's upcoming treatment session(s).

It may be an advantage of the present disclosure to provide another method for determining at least one treatment modality of a dialysis treatment of a specific patient, or a dialysis accompanying treatment, and a device for executing this method. A further advantage of the present disclosure may be to specify a treatment apparatus, a treatment modality to be used for controlling a treatment or an apparatus and the computer-related means for executing the method.

SUMMARY

These advantages are provided by the method for determining at least one treatment modality of a dialysis treatment of a specific patient and the device and the treatment apparatus having features as disclosed. Furthermore, these advantages may be provided by using a treatment modality according to the present disclosure. Moreover, these advantages may be provided by the digital storage unit, the computer program product, and the computer program according to the present disclosure.

The method according to the present disclosure is a method for determining at least one treatment modality of or for a dialysis treatment of a specific patient for which a dialysis fluid or liquid or dialysis solution, e.g., a peritoneal dialysis solution, will be used.

The method encompassing providing or reading in at least one value out of a group that consists of values as set forth below which could also referred to as "input values" as they are required for starting the method in the first place.

The first value of that group reflects the fluid status, e.g. the overhydration ("OH") of the patient. The second value reflects the salinity or osmolarity of the patient, e.g., in the blood, in the urine or in another body tissue or body fluid such as saliva. The third value reflects the blood pressure of the patient. The fourth value reflects the renal function of the patient. The fifth value reflects a heart issue the patient may have. The sixth value relates to hypotension, the seventh value reflects vessel conditions such as stiffness of a vessel (e.g., a blood vessel), the eighth value is a total protein content of the patient (of, e.g., more than 7 g/liter).

The method further encompasses handing down at least one treatment modality for a treatment, e.g., an upcoming or future treatment. In doing so, at least one value of the group is taken into account or considered, e.g., as an input variable for an algorithm or as a value to be compared with reference material, e.g., stored reference tables, stored material from previous treatments (e.g., treatments of the same patient), input by the doctor or the like. The algorithm and the reference material may be configured to consider one, two, or more of above-mentioned values or dimensions at the same time.

"Handing down a treatment modality" may be outputting, pre-determining, calculating, looking-up and/or setting a treatment modality. The treatment modality may be referred to as the result or the output of the method according to the present disclosure.

A "treatment modality" may be information or a value reflecting one parameter of a dialysis treatment. Examples of modalities have been given above. They encompass a flow conveyed by a pump, a volume and/or concentration of a commercially available substance used during dialysis such as a dialysis fluid (e.g., dialysis solution), a substitution fluid, a peritoneal dialysis solution, a drug, a solution type, and the like.

The device according to the present disclosure is configured to carry out the method according to the present disclosure. It can be a controller, a computer, a programmable hardware device, etc. It may comprise appropriately configured or programmed software or a source code or codes.

The treatment apparatus according to the present disclosure is a dialysis apparatus having or consisting of some or all treatment devices needed for treating patients with impaired renal function using a dialysis liquid, such as a control device for controlling its operation, pumps, valves, tubings, a peritoneal dialysis organizer and/or filters and the like. The treatment is configured to compensate at least in part for the lost renal function.

The treatment apparatus comprises or is connected to either a device according to the present disclosure or to a control or closed-loop control device (herein in short: "control device" means both control devices and closed-loop control devices), which is configured to execute the method according to the present disclosure. Alternatively, or additionally, it is connected to or comprises a device according to the present disclosure.

The device or the treatment apparatus may comprise components configured for carrying out one, more or all steps of the method according to the present disclosure. For example, a unit or a device configured for providing/reading at least one input value and a component for determining or setting at least one treatment modality for a treatment, may be part of either the device or the treatment apparatus. Similarly, a device configured for carrying out a particular step of the method may be part of the device or the treatment apparatus, e.g., a storage unit for storing a suggested treatment modality.

The treatment modality according to the present disclosure serves for treating a patient using a treatment apparatus having treatment devices, such as pumps, tubings or valves, for treating a patient using a dialysis liquid. The treatment modality is calculated or set based on the method according to the present disclosure.

As stated before, the treatment modality can be a drug or its dosage recommended by the method according to the present disclosure. Hence, the dosage may also define a treatment modality for the specific patient, the salinity or osmolarity of a dialysis solution used, the number of bags (bags per day) having a particular sodium ("Na") concentration, a bag from a set bags having different sodium concentrations, and the like.

The treatment modality can be a proposed use of a drug, e.g., a diuretic, as similarly described below.

The digital storage unit can be, e.g., a hard disc drive, CD or DVD, a memory card (e.g., an SD card) that has electronically readable control signals, which are able to interact with a programmable computer system such that a method according to the disclosure will be executed.

The computer program product according to the disclosure has a program code stored on a machine-readable data medium for executing a method according to the disclosure when executing the program product on a computer.

According to the present disclosure a computer program product can be understood as, for example, a volatile signal, a computer program which may be stored on a storage unit, an embedded system as a comprehensive system with a computer program (e.g. an electronic device with a computer program), a network of computer-implemented computer programs (e.g., a client-server system, a cloud computing system, etc.), or a computer on which a computer product is loaded, executed, saved or developed.

The term "machine-readable data medium" as used herein denotes in certain embodiments according to the present disclosure a medium containing data or information, which is interpretable by software and/or hardware. The medium may be a data medium, like a disk, a CD, DVD, a USB stick, a flashcard, an SD card or the like.

A computer program according to the present disclosure can be understood as, for example, a physical, ready-for-distribution software product which comprises a computer program.

The computer program according to the disclosure has a program code for the execution of a method according to the disclosure when executing the program on a computer.

That all or some of the machine-executed steps of the method according to the present disclosure are prompted or executed also applies to the digital storage unit according to the present disclosure, the computer program product according to the present disclosure and the computer program according to the present disclosure.

Whenever numbers are mentioned herein, the skilled person understands these to be a lower limit. The person skilled in the art would thus read, e.g., "at least one" instead of "one," assuming this does not present a contradiction or inconsistency as recognised by the person skilled in the art. This interpretation is comprised by the present disclosure just as much as the interpretation that a number, such as "one," means precisely and exclusively that number, such as "exactly one," wherever this is physically possible as recognized by the person skilled in the art. Both interpretations are comprised by the present disclosure and both are valid for all numbers mentioned herein.

In the following, the use of the expression "may be" or "may have" and so on, may be understood synonymously with "in exemplary embodiments is" or "in exemplary embodiments has," respectively, and so on, and is intended to illustrate exemplary embodiments according to the present disclosure.

Whenever the terms "programmed" or "configured" are mentioned herein, it is thus disclosed that these terms are interchangeable.

"Determining" as used herein may also be understood as pre-determining, calculating, handing down and/or setting.

Whenever a suitability or a method step is mentioned herein, the present invention encompasses a corresponding programming or configuring of a suitable apparatus or a section thereof as well as apparatuses programmed in such a manner.

Whenever an embodiment is mentioned herein, it is an exemplary embodiment according to the present disclosure.

"User" as used herein may be a doctor, medical staff or a patient.

Regarding the fifth value reflecting a heart issue the patient may have, a classification whether the patient has a heart issue at, and if so, how severe it is, may be analogous to the New York Heart Association (NYHA) Functional Classification. It places patients in one of four categories based on how much they are limited during physical activity.

Regarding the sixth value relating to hypotension, a hypotension at a systolic blood pressure below 100 mmHg may, e.g., be considered as equivalent to NYHA class II.

Regarding the seventh value relating to vessel conditions such as stiffness of a vessel (e.g., a blood vessel), criteria known from the peripheral arterial occlusive disease might apply here as well.

Whenever sodium ("Na") is mentioned herein, this comprises sodium as well its derivatives, solutions and salts as long as this does not lead to a contradiction as recognised by the person skilled in the art.

Embodiments according to the present invention may encompass some or all of the features mentioned infra or supra in any arbitrary combination provided such a combination be not recognised by the person skilled in the art to be technically impossible.

The blood pressure value may have been taken or measured by any blood pressure taker known to those skilled in the art. The blood pressure taker may comprise an inflatable blood pressure cuff. It may be configured to output measurement results or information to the device or to the treatment apparatus, optionally in a wireless manner.

As regards a suitable definition of overhydration (OH) reference is made to WO 2006/002685 A1 where overhydration is defined or calculated as follows:

$$OH=a*ECW+b*ICW+c*\text{body weight}.$$

The respective disclosure of WO 2006/002685 A1 is hereby incorporated by way of reference. It is to be understood that OH can be determined in different ways, all of which are known to the person skilled in the art. One of those methods comprises measuring a dilution and calculating the OH value based thereon. Also, suitable, exemplary methods are disclosed in EP 1 763 316 B1 and EP 2 578 147 B1, the respective disclosures of which are incorporated by reference.

The overhydration value may have been measured by a method known as bioimpedance spectroscopy (BIS).

In particular, the overhydration value may have been measured using a "Body Composition Monitor" (BCM) available from Fresenius Medical Care Deutschland GmbH or Fresenius Medical Care AG & Co. KGaA, both residing in 61346 Bad Homburg v. d. H., Germany.

The sodium concentration may have been measured in, e.g., blood serum, blood samples, urine, or body tissue. Optical or chemical analysis methods are known to the skilled person. Also, the concentration of sodium may be measured by magnetic resonance imaging methods as is known to the skilled one.

Further, if a blood sodium concentration is stated herein it refers to the blood serum sodium without limiting the invention to the serum concentration.

The glomerular filtration rate may have been estimated by the MDRD-formula (Modification-of-Diet-in-Renal-Disease-Study) with, e.g. four or six variables, or, possibly even more precise, by the formula suggested by the CKD-EPI (Chronic Kidney Disease Epidemiology Collaboration).

The eGFR may be estimated by the Cockroft-Gault-formula. Also, it is referred to WO 2016/151087 which also discloses methods for calculating the eGFR. Its respective disclosure is incorporated into the present specification by way of reference.

sodium dialysis concentration, or lower than 120 mmol/l, e. g. 112 mmol/l.

Also, besides selecting a suitable dialysis solution, e.g., a low-sodium solution for the patient, an overhydration of the patient can be avoided and alleviated by selecting a suitable glucose solution, and also by considering both the fluid status of the patient (see table below) and the membrane status, function or permeability of the peritoneum.

| Fluid status Membrane function | Membrane normal | Membrane Leaky (high hydraulic conductance) | Membrane restricted (interstitial fibrosis, aquaporin loss/low hydraulic conductance) |
|---|---|---|---|
| Dehydrated | 1.5% Glucose (1.5% Balance Solution) | 1.5% Glucose (1.5% Balance Solution) | 1.5% Glucose (1.5% Balance Solution) |
| Normohydrated (euvolemia) | 1.5% Glucose (1.5% Balance Solution) | 2.5% Glucose (2.5% LoNatra Solution) | >= 3.86% Glucose (3.86% LoNatra Solution) |
| Mild overhydration | 2.5% Glucose (2.5% LoNatra Solution) | >=3.86% Glucose (3.86% LoNatra Solution) | 7.5% Glucose (7.5% Icodextrin, 1 bag) |
| Severe overhydration | >=3.86% Glucose (3.86% LoNatra Solution) | 7.5% Glucose (7.5% Icodextrin, 1 bag) | 7.5% Glucose (7.5% Icodextrin, 1 bag) |

Dialysis solution may be used either from containers (e.g., bags) or may be mixed by the dialysis apparatus from water and liquid or dry concentrates. In some embodiments, the step of determining the at least one treatment modality is or encompasses determining or setting a number of bags (or containers) containing dialysis liquid to be used within a pre-defined period of time such as "per day", wherein the solution contained in these bags has a specific salinity or osmolarity, e.g., a specific sodium content or concentration. The specific sodium content or concentration may be low, or low when compared to other solutions or bags, and therefore bags comprising such low sodium solution are addressed as "low sodium bags."

In particular embodiments a low sodium solution contains less than 135 mmol/l, or less than 133 mmol/l of sodium.

Solutions having following features qualify as examples of low sodium solutions as referred to herein:

1: Low: Balance Low Sodium

Na: 125 mmol/l (Na: 125 mmol/l; Chloride: 91.5 mmol/l)

| Osmolarity [mOsmol/l] | 338 | 381 | 491 |
|---|---|---|---|
| Glucose [%] | 1.5 | 2.3 | 4.25 |

2: Very Low: Gambro PD Sol

Na: 112 mmol/l (Na: 112 mmol/l; Chloride: 74.8 mmol/l)

| Osmolarity [mOsmol/l] | 340 |
|---|---|
| Glucose [%] | 2 |

In general, a sodium concentration of the dialysis solution used within the frame of the present disclosure may range between 100 mmol/1 and 150 mmol/l. The low sodium concentration may comprise sodium in a concentration between 120 and 135 mmol/l, or between 122 and 133 mmol/l. In contrast, very low sodium dialysis solution may comprise sodium in any concentration lower than the low Clinical practice guidelines suggest the use of Icodextrin only in patients experiencing difficulties maintaining euvolemia due to insufficient peritoneal ultrafiltration, especially those with high and average peritoneal transport.

The low sodium bags may be selected from a multitude of (e.g., at least two) bags with different salinities, osmolarities or sodium concentrations or contents.

In some embodiments, a combination of a normal sodium solution combined with a low sodium solution and a very low sodium solution is suggested. For example, a Balance solution may be combined with a "LoNatra" solution and a "Gambro PD sol" solution or with solutions having comparable respective sodium concentrations.

In some embodiments, a combination of a normal-sodium solution combined with a very low sodium solution is suggested.

In several embodiments, the step of determining the at least one treatment modality is or encompasses, quantitatively and/or qualitatively, determining the salinity or the sodium content or concentration, or a concentration of glucose and/or another osmotic agent, of the dialysis liquid to be used in the upcoming treatment of the specific patient. The dialysis liquid may be provided in bags.

Although sodium is mentioned herein on several occasions, the salinity or osmolarity is not necessarily determined by the concentration or content of sodium comprised by the dialysis solution. Rather other electrolyte concentrations ($Na^+$, $K^+$, $Ca^{2+}$, $Mg^{2+}$, $Cl^-$, $Fe^{2+}$, $Fe^{3+}$ etc.) may in some embodiments also be considered, be it in addition or alternatively.

In some embodiments of the method, the step of determining the at least one treatment modality is or encompasses setting the use of a diuretic (or requesting not to use diuretics, depending on the findings and the output of the method according to the present disclosure, also see below) or glucose and/or another osmotic agent, e.g., its concentration, the point of time when it is to be administered, the frequency of its administration, and the like.

Also, a qualitative value may qualify as a treatment modality set by the present method. For example, such qualitative value may be, or encompass, the conclusion that the drug in question should not be prescribed, ingested or administered for a patient based on his/her parameter input values at issue.

In several embodiments, the treatment modality or modalities determined, set or output by the method are saved or stored in a storage unit which can be part of the device or of the control device of a treatment apparatus.

In some embodiments, the control device of the treatment apparatus is configured to monitor, effect, start, modify and/or execute a treatment of a patient in interaction with corresponding treatment devices of the treatment apparatus (such as pumps, valves, and the like) based on, or while taking into account, the at least one treatment modality determined by the method according to the present disclosure.

In some embodiments, the treatment apparatus according to the present disclosure comprises a display unit. The control device of the treatment apparatus is configured to display the treatment modality output by the method.

For example, the display unit can be configured to display to the user which kind of bag of dialysis liquid has to be used, e.g., used next, or which kind of bag or other treatment modality is requested in the treatment of the specific patient who is the patient whose input values comprised of the above-mentioned group of values have been considered by the control device when running or executing the method according to the present disclosure.

Particularly, the control device may be configured to display the value of the salinity or the sodium content of the dialysis liquid bag to be used or used next and/or the volume to be administered in the course of the treatment.

For example, the display may be configured for displaying the kind of bag with dialysis solution to be used next in the treatment of the patient as an example of a treatment modality displayed, or the number of bags with low sodium concentration and/or the volume to be administered or prepared.

In several embodiments, the treatment apparatus comprises a confirmation unit. The confirmation unit may be configured to require and to accept the user's confirmation. That is, the user may have to confirm that he/she has been informed about the treatment modality output shown on the display unit.

The confirmation unit may be configured to accept the user's confirmation via, e.g., a button, a switch, an input means, a touch screed field, or the like.

The control device of the treatment apparatus or an inhibiting unit of the device according to the disclosure may be configured to not allow a treatment unless or until the user confirms or has confirmed that he/she has noticed the treatment modality displayed by the treatment apparatus. The means for not allowing (e.g., preventing or inhibiting) the treatment to be started or to continue until the user has confirmed that he/she has noted the displayed treatment modality may comprise or consist of, for example, means for blocking or not starting a pump, e.g. the pump for conveying the dialysis liquid.

In some embodiments, the control device of the treatment apparatus according to the present disclosure is configured to not allow a treatment unless or until the user informs the treatment apparatus that a bag of the requested or displayed kind has been provided to be used with the treatment apparatus, e.g. by pressing a confirmation button or the like, or that the treatment modality has been considered or already set or provided for in any other way by the user.

In some embodiments, the method is a computer-implemented method.

In some embodiments, the method may use stored as well as presently inputted values for determining or outputting a treatment modality.

In certain embodiments, the input values for the method have been directly measured. In addition, or alternatively, the value may have been derived indirectly from other values, which allow a sufficient approximation of the respective value.

The sodium concentration can also be measured and/or transmitted to a central server directly before the treatment or prior to that, e. g., on the day before the treatment. Then a new prescription can be downloaded and accepted.

In some embodiments, the method provides treatment modality settings or determinations as recommendations.

In some embodiments, the method is carried out in the device according to the present disclosure.

In some embodiments, providing or reading at least one value out of the group of "input values" does not include the measuring step necessary to arrive at the input values. Rather, the values to be provided or read have all been gathered before the method according to the present disclosure may start at all. In these embodiments, the input value can be referred to as "pre-determined."

Herein, when it is stated that any device or unit "allows the performance of" or "may perform" a certain function etc., this comprises the interpretation that the unit or device in question is configured to perform such function.

In some embodiments, the device according to the present disclosure is connected or connectable to the treatment apparatus, e.g., in the sense of an internet of things concept (IoT).

In some embodiments, at least two elements out of the group consisting of the device, the treatment apparatus and the devices for measuring the input values (such as the blood pressure taker) are connected or connectable in a wired manner and/or via a wireless network (e.g., WiFi or Bluetooth) to at least one further element of this group.

In some embodiments, the device is stationary or mobile. In some embodiments, the device and the treatment apparatus may be physically separate, but functionally connected or connectable to each other, e.g., an output means of the device.

In some embodiments, the device can be a hand-held device such as a smartphone, a Blackberry or the like. It can optionally be in communication connection with the control device or a computing unit of the treatment apparatus.

In some embodiments, the device or the treatment apparatus provides the treatment modality recommendation via an output unit such as a display and/or a printer. A display may be a simple number display, an LCD (e.g., allowing detailed display of data) or the like. Additionally, or alternatively, the device may provide the treatment modality recommendation remotely, e.g., via a wired or wireless network and/or via broadcast of electromagnetic waves and/or light. It might comprise a transfer unit for this.

The device or the treatment apparatus may incorporate a web server such that a user may interact with the device, e.g., via a web browser. The web server may allow providing input values to the device and/or receiving treatment modality recommendations.

In some embodiments, there can also be a measurement device at the patient's home for receiving the input values.

In some embodiments, the device and/or the treatment apparatus allows the transmission of data to the device and/or from the device to the user via speech. To this end, the device comprises a speech output unit and/or a speech recognition unit. This may be particularly useful for blind or sight-impaired patients.

In some embodiments, the device and/or the treatment apparatus has a data reader. In some embodiments, a data reader may read data from an information containing item that contains patient identification data. Such an item could be a patient ID card. The reader may in some embodiments read a patient's ID number from the item. The item may in some cases be a card, e.g., a smart card, a bracelet, a tag or a fob. The reader may use contactless or contact technology to read information from the item. The item may contain a magnetic strip containing information. The item may contain an integrated circuit, which contains information. The reader may read the card using, e.g., near field technology or by physically touching electric contacts on the card, which are connected to an integrated circuit on the card. In some embodiments, the item comprises a one-dimensional or a two-dimensional bar code, which contains patient information.

In some embodiments, the data reader can read biometric information. For example, some readers may be able to identify patients by their fingerprints.

The data reader may comprise a keyboard, a scanner, such as a barcode scanner, a camera, a magnetic strip card reader, an RFID tag reader, a near field communication reader and/or writer.

In some embodiments, the card to be read by the reader of the device contains a patient identification number. In other embodiments, the item—additionally or alternatively—contains information concerning laboratory results, vital data, current and/or previous prescription dosages and/or dates of past doctor visits and/or treatment protocols. In some embodiments, the device may process the data stored on the card to recommend a certain drug dosage. Additionally, or alternatively, the device may use the patient's ID to recall data from an internal database or from a database to which the device is connected, preferably via a network.

In some embodiments, the device and/or the treatment apparatus may contain a processor, a volatile and/or a non-volatile memory unit. The non-volatile memory unit may contain software, which implements at least one part of the method.

In some embodiments, the device or parts of the control device of the treatment apparatus may be updateable. Preferably, a non-volatile memory in the unit may be partially or entirely overwritable with new information. In this way, it may be possible to change the method to adapt to new circumstances, knowledge, algorithms or parameters.

The device or parts of the device of the treatment apparatus may also receive updates by a remote software update mechanism, e.g., via the internet or private networks. They may be designed such that an update may be propagated from a central server and/or peer-to-peer. Furthermore, they may be updateable using the data reader mentioned above. Updateable may also mean measurements executed directly before the treatment.

In some embodiments, the device is integrated into, connectable or connected to an apparatus, which may provide health information. Such an apparatus may be used in diagnosis or therapy of a patient. Such an apparatus may comprise sensors to acquire patient data and/or may contain treatment parameters for the treatment of the patient. Such an apparatus may be the treatment apparatus according to the present disclosure.

In some embodiments, the method is based on an algorithm to suggest the treatment modality in order to arrive at the optimal therapy.

In some embodiments, the method is based on an algorithm stored in the device, in the dialysis apparatus itself or in a server computer that communicates with the treatment apparatus, e.g., via an internet connection.

In some embodiments, specific upper limits of the number of low sodium bags, or of the volume to be used, and/or lower limits of the sodium concentration of the dialysis solution may be imposed by the method.

In some embodiments, the treatment modalities suggested by the method may not become actual prescriptions without external medical intervention. In this case, the method is merely an aid to the doctor or the patient, the output of which the doctor or patient may follow or ignore. The use of the method then involves clinical supervision and control action such that clinical specialists only prescribe the relevant drug or peritoneal dialysis solution after receiving the output of the method as well as the patient's clinical condition.

In some embodiments, the method does not formulate treatment modality prescriptions autonomously, but only provides suggestions to doctors.

In some embodiments, the method or the device does not administer any kind of substance or start any treatment directly.

In some embodiments, erroneous, inconsistent or unusual data and/or data indicating danger to the patient may be detected. In these cases, the method may indicate these to the user, e.g., by providing an alert.

In some embodiments, no treatment modality suggestion is produced if the input data is incomplete and/or inconsistent.

In some embodiments, the method consults an external database periodically to check the available drugs and/or their dosages and/or the recommendations of the current guidelines.

In some embodiments, the device and/or the treatment apparatus according to the disclosure includes a treatment modality transfer unit that is configured to transfer data such as the suggested treatment modality between the controller or the control software of the treatment apparatus and the device. The transfer may be wired or wireless, such as via internet, cloud, phone, or the like.

In some embodiments, the device or the treatment apparatus according to the disclosure comprises a software configured to be used by the doctor to develop a therapy scheme and/or to store treatment parameters (such as dialysis modalities, dialysis solution type, treatment time and frequency, ultrafiltration or fill volume, and the like). Such software solutions are, e.g., marketed as PatientOnLine—PD-Management-Software by Fresenius Medical Care Deutschland GmbH or Fresenius Medical Care AG & Co. KGaA, both residing in 61346 Bad Homburg v.d.H., Germany.

In some embodiments, software for carrying out the method according to the present disclosure is integrated into or combined with such patient management software solutions.

In some embodiments, the output of the method according to the present disclosure is written on and read from a card or smart card containing patient data, e.g., a card as set forth in more detail supra.

In some embodiments, the treatment modality is a treatment parameter.

In some embodiments, the treatment apparatus is a peritoneal dialysis machine, an automatic peritoneal dialysis cycler (APD-cycler), a continuous ambulatory peritoneal dialysis system (CAPD system), a haemodialysis machine, a haemofiltration or a haemodiafiltration machine.

One or several of the herein mentioned advantages may be achieved by some embodiments according to the present disclosure.

All or some of the advantages of the method as mentioned above may apply to the device and the treatment apparatus according to the disclosure and vice versa.

By employing the method according to the disclosure, doctors may achieve better results in treating patients with renal dysfunctions.

In general, using low sodium dialysis solutions can reduce sodium and/or fluid overload. Prescribing low sodium dialysis solutions where not appropriate may result, however, in severe adverse effects. The present disclosure helps to distinguish between those patients who will benefit from low sodium solutions from patients who will not benefit or, worse, suffer from low sodium solutions, e.g. from blood pressure drops.

Similarly, the present disclosure may distinguish between patients who benefit from Icodextrin or similar drugs from those who do not benefit or who are expected to actually suffer from taking or being given Icodextrin. The same could apply for the use of diuretics.

The device may more successfully consider all the relevant factors and process larger amounts of data than is feasible for a human being.

Thus, the method may yield better treatment modality recommendations such as drug dosage recommendations or recommendations related to the use of low sodium dialysis solution, or the like. "Better" may here be understood to mean that, when such better recommendations are followed, the patient receives a more appropriate treatment than when a physician prescribes or choses the treatment modality according to his gut feeling or according to known but possibly far from perfect guidelines. In fact, in many cases, available guidelines hitherto known do not lead to uniform success for all patients.

CAPD systems operate purely gravimetrically and are operated manually or automatically. Also, there are semi-gravimetrical systems. None of the aforementioned systems do require any complex equipment in terms of equipment technology. These systems are therefore simple and inexpensive to manufacture and operate and are virtually trouble-free and maintenance-free in comparison with other dialysis machines. However, these systems require a high level of personal responsibility and discipline on the part of each patient in performing the treatment, for example in choosing the correct or the best suited dialysis solution. The method according to the present disclosure may assist the patient in this as it suggests suitable treatment modalities in the light of the particular patient's physical conditions such as overhydration and blood sodium concentration.

Peritoneal dialysis machines are not equipped to provide feedback to the patient or doctor regarding the effectiveness of the patient's recent treatment sessions. Hence, for monitoring the effect of the treatment modalities of interest and for adjusting them if appropriate the patient has to see his/her doctor on a regular basis. The present disclosure may alleviate this shortfall as the treatment may be adjusted regarding at least one treatment modality by the patient himself/herself based on very few input values available to the patient or by a data connection to the treating nephrologist.

The treatment, e.g., via the treatment apparatus according to the present disclosure, can be set to allow the patient to run a prescription tailored to the day's activities. If the patient exercises heavily on a certain day, losing significant amounts of body fluids via sweat, the patient may be better off with normal sodium dialysis solution that might respond well to normal dialysis liquid. If the patient is out to a social event the following night and consumes more liquids than normal, he/she may suffer severe overhydration. He/she may benefit from a low sodium solution. This can be checked by a sodium measurement directly before the treatment.

Other aspects, features, and advantages will be apparent from the description, figures, and claims.

BRIEF DESCRIPTION OF THE FIGURES

In the following, the method according to the present disclosure is described based on preferred, purely exemplary embodiments thereof with reference to the accompanied drawing.

In the drawing the following applies.

DETAILED DESCRIPTION

Figure 1:
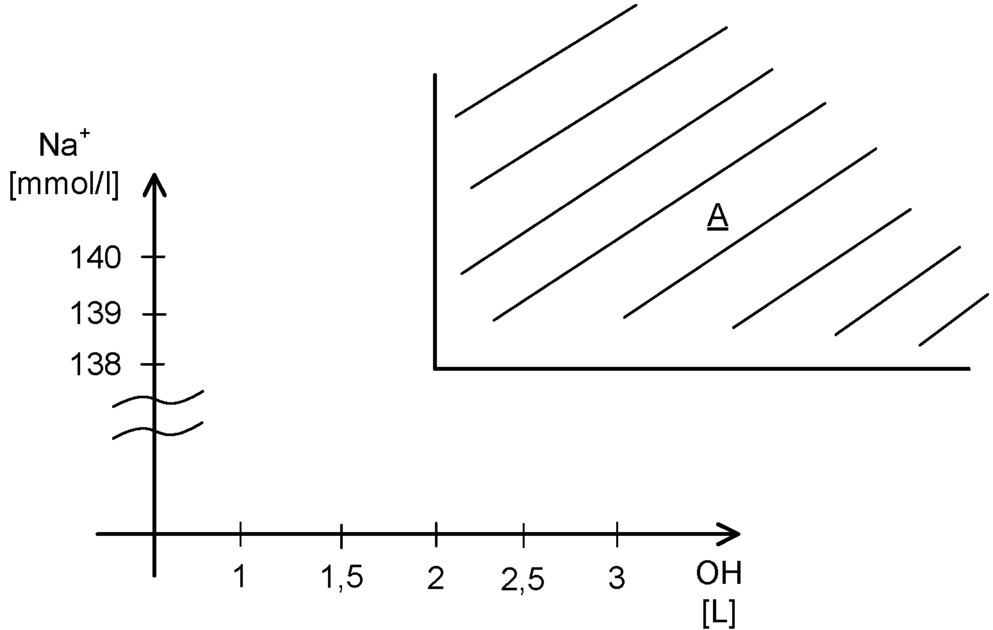
FIG. 1 shows a graphical representation of possible outcomes of the method according to the present disclosure in a first embodiment

FIG. 1 shows a graphical representation of the basis for an outcome of a first embodiment of the method according to the present disclosure.

Figure 1A:
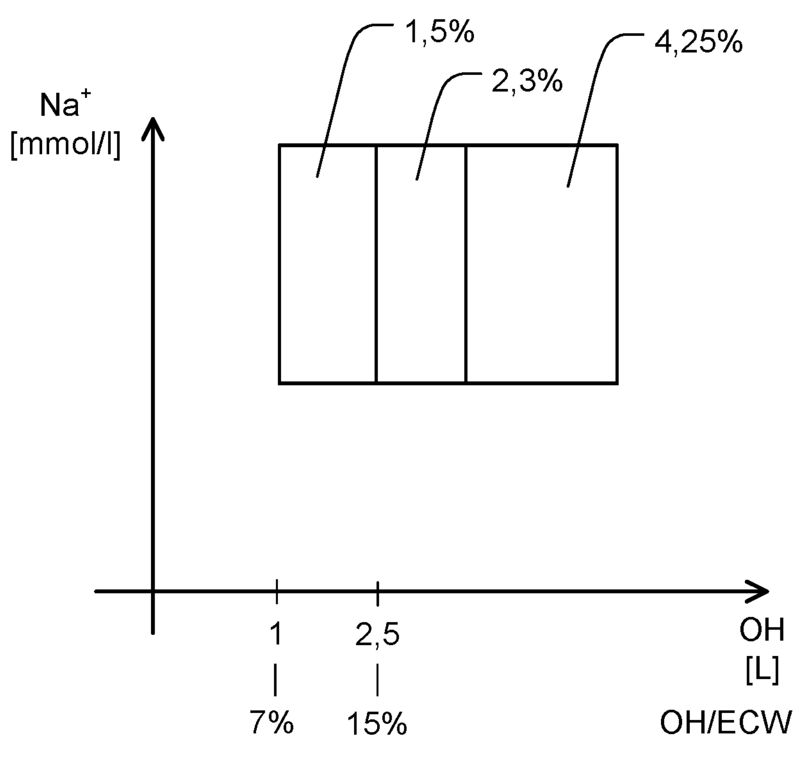
FIG. 1*a* shows a graphical representation of possible outcomes of the method according to the present disclosure in a second embodiment.
Figure 1B:
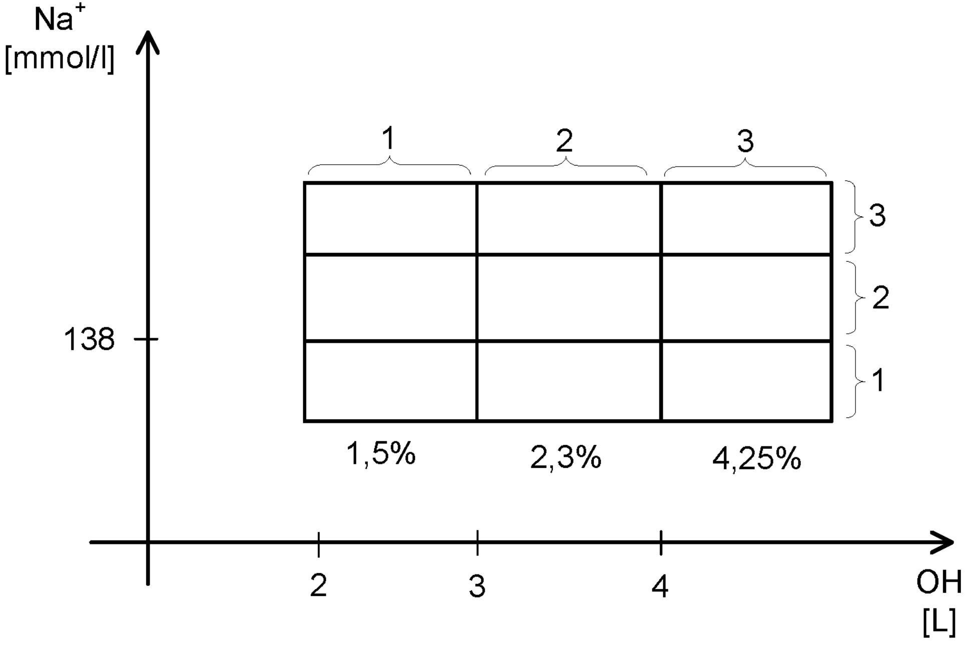
FIG. 1*b* shows a graphical representation of possible outcomes of the method according to the present disclosure in a third embodiment.
Figure 1C:
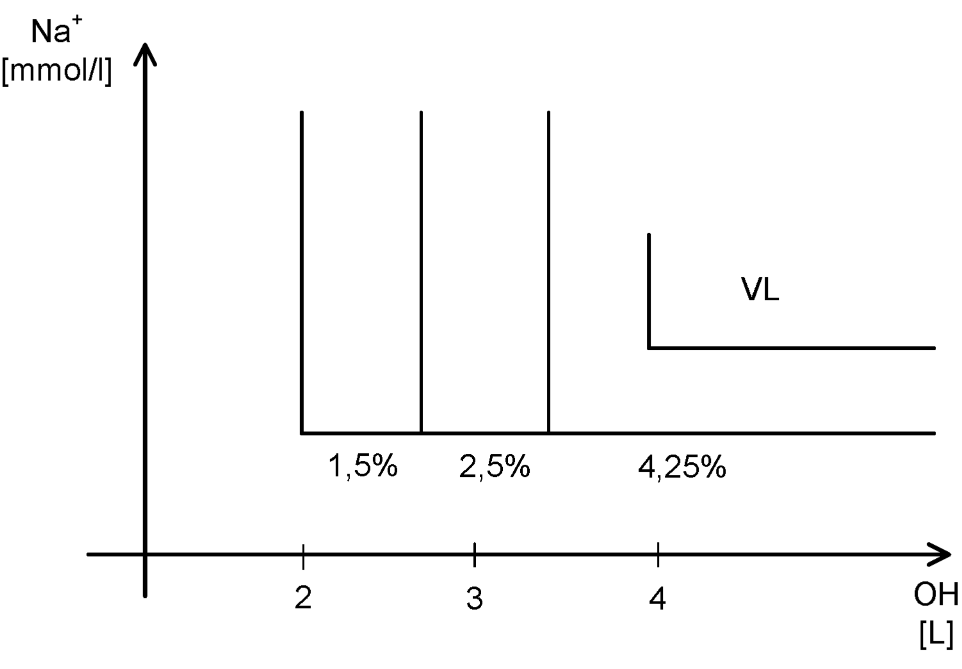
FIG. 1*c* shows a graphical representation of possible outcomes of the method according to the present disclosure in a fourth embodiment.
Figure 1D:
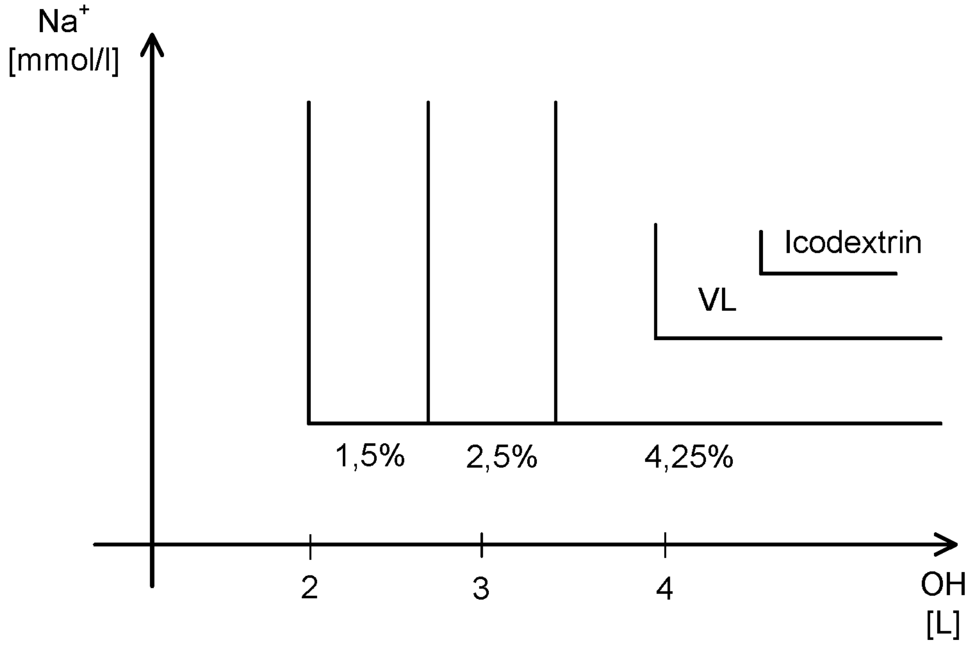
FIG. 1*d* shows a graphical representation of possible outcomes of the method according to the present disclosure in a fifth embodiment.
Figure 1E:
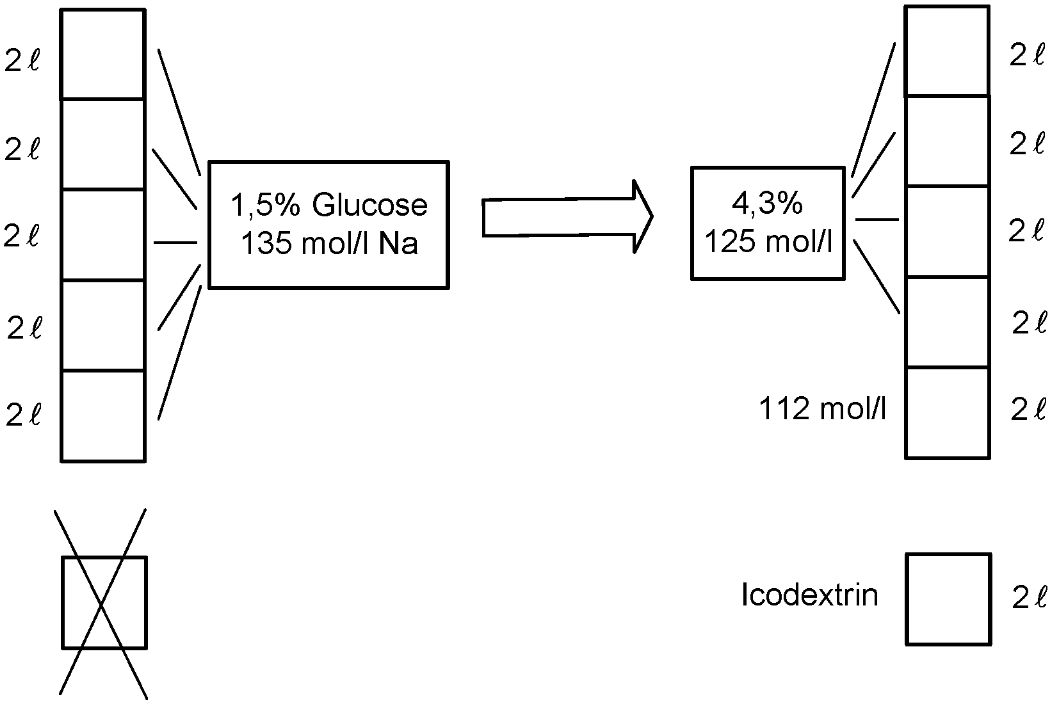
FIG. 1*e* shows a graphical representation of possible outcomes of the method according to the present disclosure in a sixth embodiment.
Figure 1F:
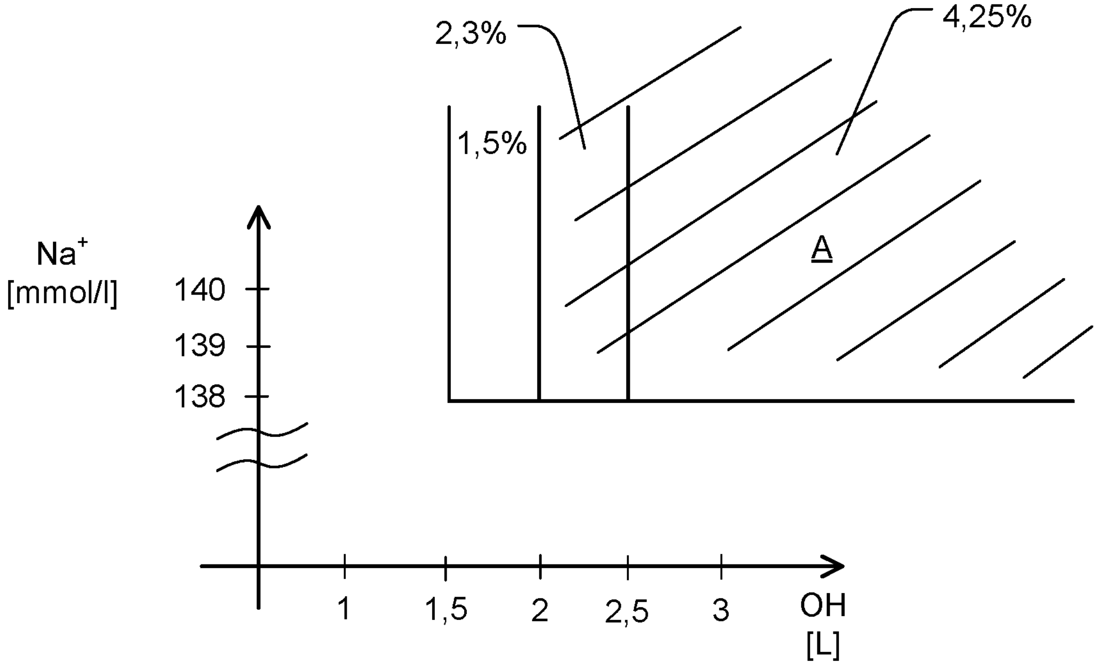
FIG. 1*f* shows a graphical representation of possible outcomes of the method according to the present disclosure in a seventh embodiment.

As can be seen from FIG. 1, after having taken both the overhydration OH values (having the dimension "liter", [L] or OH/ECW (extracellular water) which is a relative value, or indexed) and the salinity (here expressed by the blood sodium concentration having the dimension "millimole per liter", [mmol/l]) into account it is determined by the method that patients whose blood sodium is in excess of 138 mmol/l and who suffer an overhydration of at least 2 liters should be treated with dialysis using a low sodium dialysis solution or in combination with glucose solutions having different strengths or osmotic agent solutions having different strengths as is indicated in FIG. 1*f* below.

It is noted that when glucose is mentioned herein, it is referred to any drug that increases the colloid osmotic pressure such as Maltodextrin or Icodextrin (the latter being known under the trademark "Extraneal®").

The treatment modality derived from the method according to the present disclosure is, in this particular embodiment, the use of low sodium dialysis solution if the patient in question finds himself/herself in the shaded area A.

On this basis a recommendation may be made from the map itself, any other map or an algorithm.

FIG. 1*a* shows a graphical representation of possible outcomes of the method according to the present disclosure in a second embodiment.

It shows the patients sodium concentration (preferably measured in blood samples) over his/her overhydration (OH) or overhydration over the extracellular water (OH/ECW).

The treatment modality derived from the method according to the present disclosure is, in this particular embodiment, the use of glucose (without also using low sodium dialysis solution). Optional glucose concentrations are noted in FIG. 1*a* depending on the exemplary overhydration level.

FIG. 1*b* shows a graphical representation of possible outcomes of the method according to the present disclosure in a third embodiment.

FIG. 1*b* reveals three columns 1 to 3 and three lines 1 to 3.

In the embodiment of FIG. 1*b*, depending on their level of overhydration (more than 2 L, more than 3 L, more than 4 L, and so on) the patients are either treated using dialysis solution comprising, for example, 1.5% glucose, 2.3% glucose or 4.25% glucose. The specific concentrations may vary, but they should rise with rising overhydration levels.

Also, patients whose Na-level is below 138 mmol/l are treated using one bag (e. g., 2 L) of low sodium dialysis solution plus three bags (e. g., 6 L in total) of normal dialysis solution (normal with respect to their sodium concentration or "Balance solution", for example), plus the aforementioned glucose as set forth above (depending on their level of overhydration (more than 2 L, more than 3 L, more than 4 L, and so on)).

Patients whose Na-level is above 138 mmol/l (see line 2) are treated using two bags (e. g., 4 L in total) of low sodium dialysis solution plus two bags (e. g., 4 L in total) of normal dialysis solution (normal with respect to their sodium concentration or "Balance solution", for example), plus the aforementioned glucoses as set forth above (depending on the overhydration level).

Finally, patients whose Na-level is yet higher (see line 3) are treated using four bags (e. g., 8 L in total) of low sodium dialysis solution plus the aforementioned glucoses as set forth above (depending on the overhydration level).

FIG. 1*c* shows a graphical representation of possible outcomes of the method according to the present disclosure in a fourth embodiment.

As in FIG. 1*b*, the higher the overhydration level is (above, e. g., a pre-set sodium concentration), the higher the concentration of glucose has to be that is comprised in the dialysis solution. Exemplary figures are stated in FIG. 1*b* which are, however, neither limiting for the present invention when it comes to the particular level of overhydration from which on the higher glucose concentration is contemplated nor limiting with regards to the specific glucose concentration.

As can be further seen from FIG. 1*b*, a combination of both administering glucose and using (e. g., 2 L of) dialysis solution having a very low sodium or salt concentration (denoted by "VL") is also encompassed by the present invention.

This concept may also qualify as the treatment modality derived from the method according to the present disclosure.

FIG. 1*d* shows a graphical representation of possible outcomes of the method according to the present disclosure in a fifth embodiment.

The treatment modality derived from the method discussed with respect to FIG. 1*c* can be further specified by administering Icodextrin as well, as is shown in FIG. 1*d*.

FIG. 1*e* shows a graphical representation of possible outcomes of the method according to the present disclosure in a sixth embodiment.

FIG. 1*e* displays the general idea behind some of the embodiments according to the present disclosure.

The illustration of FIG. 1*e* encompasses two extremes limiting an exemplary range of possibilities for the treatment modality according to the present disclosure. FIG. 1*e* relates to an exemplary patient who shall be treated using 10 L dialysis solution which can be arbitrarily split into subvolumes of 2 L or any other volume each.

On the left side of FIG. 1*e* a possible treatment modality is shown in which the patient is treated using 5 bags (comprising 2 L each), all of which differ from normal dialysis solution. In particular, the bags comprise 1.5% glucose. Regarding their sodium concentration, they may be a normal one having, for example, 135 mmol/l sodium. What is shown on the left side may be understood as a mild extreme of a treatment modality according to an embodiment of the present disclosure. Even milder extremes, in which, for example, only one bag differs from normal dialysis solution by comprising 1.5% glucose, is also encompassed by the present invention although not embodied by the particular embodiment of FIG. 1*e*.

On the right side of FIG. 1*e* the opposite extreme is shown. The patient is treated using four bags each containing 4.3% glucose and 125 mmol/l sodium. Also, one bag may comprise very little sodium, having a very low sodium concentration of, e. g., 112 mmol/l. Also, a bag comprising Icodextrin may be used as well, e.g., for a final filling, and even as an additional filling that needs not to be contemplated in a milder treatment as can be seen on the left side (see the box crossed out).

The arrow of FIG. 1*e* linking these two extremes one to each other indicates that quite a number of stepwise amendments regarding the use of dialysis solutions (having more or less sodium, more or less glucose and the like).

Hence, FIG. 1*e* reveals different escalation levels with countless shades.

FIG. 1*f* shows a graphical representation of possible outcomes of the method according to the present disclosure in a seventh embodiment.

In FIG. 1*f*, if the patient finds himself/herself in the shaded area A, a combination of low sodium dialysis solution is suggested as in FIG. 1. In addition, the patient should be treated by using glucose (or any other suitable sugar). The glucose can be comprised by the low sodium solution dialysis solution used as from 2 L of overhydration or more, e.g., in concentrations such as 2.3%, or as 4.25% as from 2.5 L OH. However, the glucose can be administered to the patient by means of the dialysis solution used even if the dialysis solution is not low sodium dialysis solution as is shown for OH levels above 1.25 but below 2 L.

Hence, the treatment modality derived from the method according to this particular embodiment of the present disclosure is the use of both low sodium dialysis solution and glucose if the patient in question finds himself/herself in the shaded area A, and to use glucose without caring for low sodium dialysis solution if the patient finds himself/herself in an overhydration below a pre-set threshold.

Figure 2:
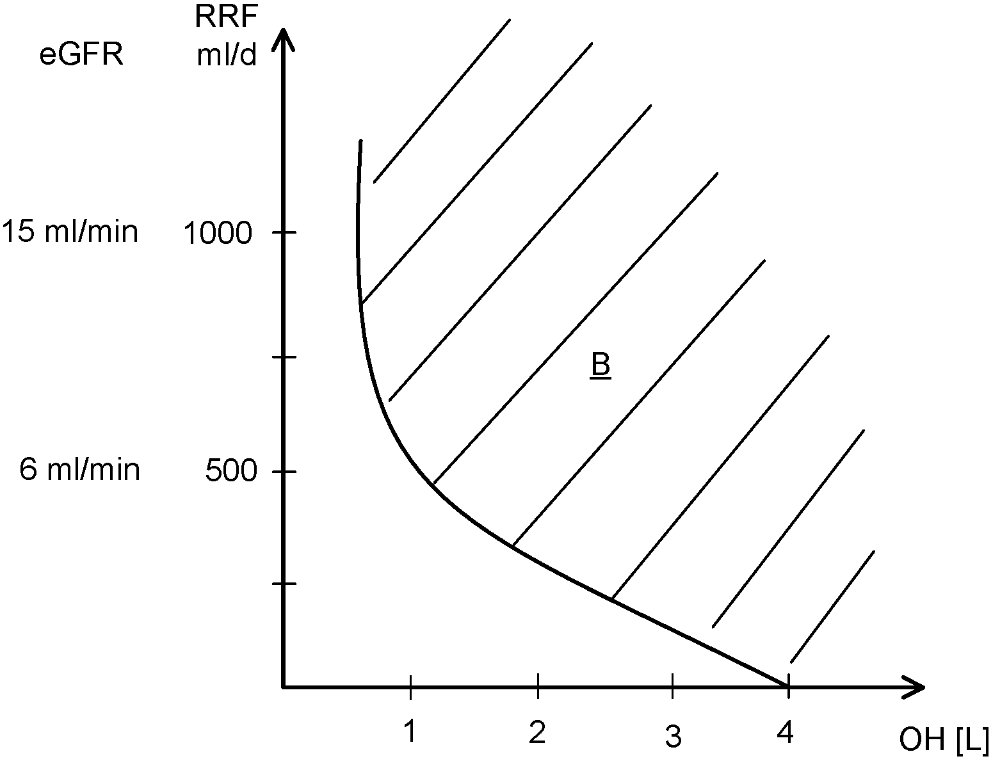
FIG. 2 shows a graphical representation of possible outcomes of the method according to the present disclosure in an eighth embodiment.

FIG. 2 shows a graphical representation of the basis for an outcome of an eighth embodiment of the method according to the present disclosure.

As can be seen from FIG. 2, after having taken both the overhydration OH values (having the dimension "liter", [L] or OH/ECW (extracellular water) or indexed) and the urine output, the residual renal filtration rate (RRF) or the estimated glomerular filtration rate (eGFR) into account it is determined by the method that patients who suffer from a predetermined level of overhydration of at least 0.5 liters and whose RRF or eGFR is in excess of a given limit varying with the level of overhydration (see the shaded area B beyond the exemplary curve of FIG. 2) should be treated with dialysis using a drug that increases the colloid osmotic pressure such as Maltodextrin or Icodextrin (the latter being known under the trademark Extraneal®) or glucose.

The treatment modality derived from the method according to the present disclosure is, in this particular embodiment, the use of the drug if the patient in question finds himself in the shaded area B.

However, although not indicated in FIG. 2, a combination of a colloid osmotic drug as, e.g., set forth above, and low sodium dialysis solution is possible as well. For example, low sodium dialysis solution can be envisaged in addition to the colloid osmotic pressure effective drug referred to in FIG. 2. The same holds true for any other embodiment, e.g., for those shown in the drawings.

Figure 3:
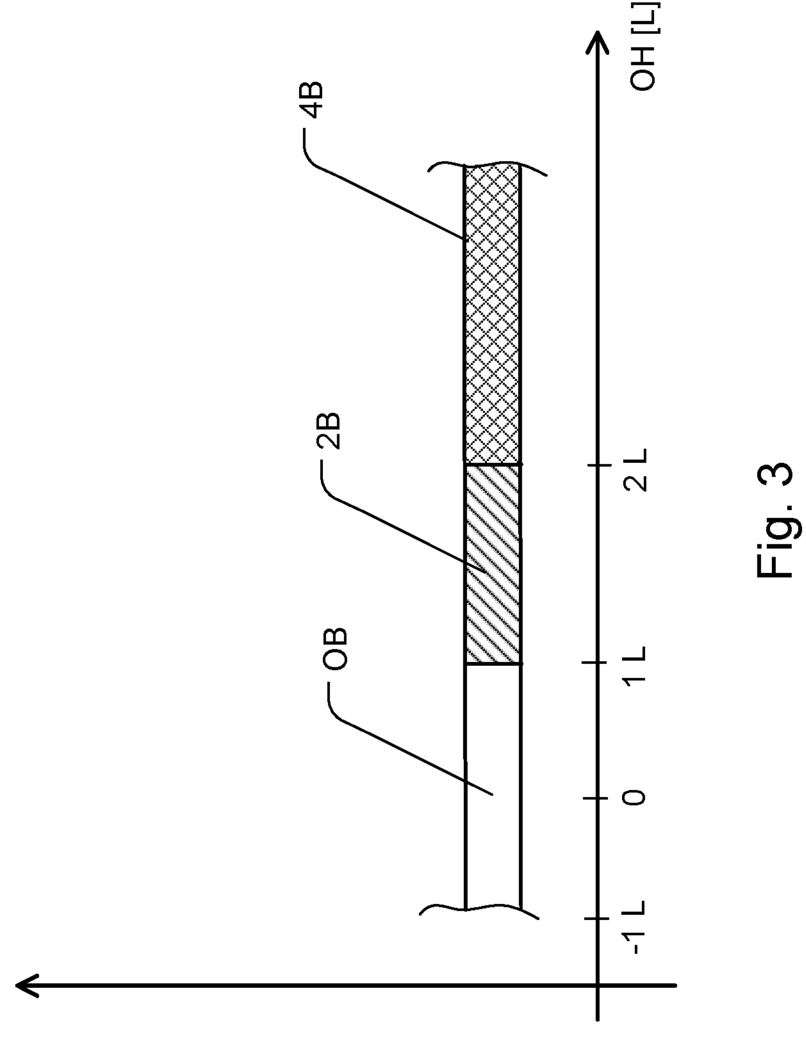
FIG. 3 shows a graphical representation of possible outcomes of the method according to the present disclosure in a ninth embodiment.

FIG. 3 shows a graphical representation of the outcome of a ninth embodiment of the method according to the present disclosure.

In this embodiment it is assumed that the low sodium solution for, e.g., peritoneal dialysis patients is provided in bags of a known size or volume. Also, a combination of low sodium but one of a multitude of different glucose concentrations may be considered in this embodiment.

As can be seen from FIG. 3, the method according to the present disclosure has revealed that the patient at issue should be treated with as many as four bags (denoted as 4B in FIG. 3) of low sodium solution optionally in combination with different glucose concentrations for example as shown in FIG. 1*a* to 1*d* per day or as long as his/her overhydration OH exceeds 2 liters (see area 4B standing for four bags), with only 2 such bags per day if the overhydration OH amounts to less than 2 liters but exceeds 1 liter (see area 2B standing for two bags), and without using low sodium bags at all if the overhydration OH is below 1 liter (see area 0B standing for no bags).

Also, using no bags of low sodium dialysis solution followed by 4 bags of normal dialysis solution (Balance solution, for example), or 2 bags of low sodium dialysis solution followed by 2 bags of normal dialysis solution (Balance solution, for example), or 4 bags of low sodium dialysis solution followed by no bags of normal dialysis solution (Balance solution, for example), or other regimens, are contemplated by the present disclosure. Those bags might come along with glucose in a variety of concentrations as explained herein.

Figure 4:
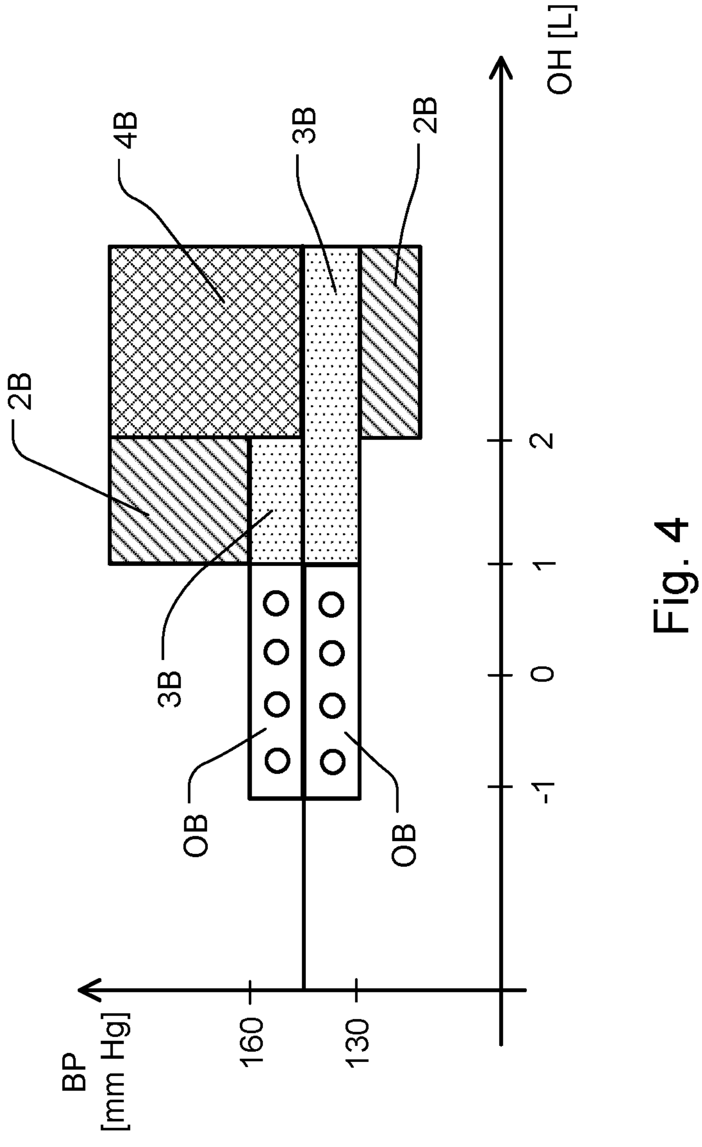
FIG. 4 shows a graphical representation of possible outcomes of the method according to the present disclosure in a tenth embodiment.

FIG. 4 shows a graphical representation of the basis for an outcome of a tenth embodiment of the method according to the present disclosure. Again, it is assumed that the low sodium solution is provided in bags of a known size or volume.

As can be seen from FIG. 4, the method of this embodiment reveals the number of bags containing low sodium solution that should be used for treating the patient. Depending on the blood pressure BP as one input value and the overhydration OH as another input value the doctor or the patient may learn from the look-up diagram of FIG. 4 how many bags of low sodium or in combination with different glucose concentrations, for example, as shown in FIG. 1*a* to 1*d*, should be used in the treatment of the patient.

Figure 5:
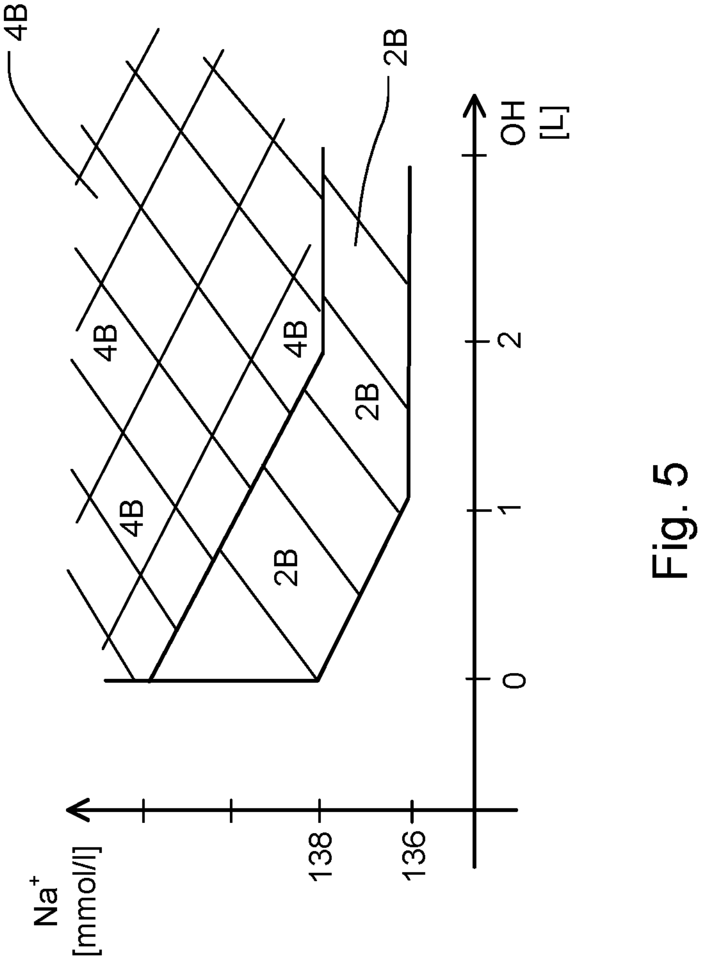
FIG. 5 shows a graphical representation of possible outcomes of the method according to the present disclosure in an eleventh embodiment.

FIG. 5 shows a graphical representation of the basis for an outcome of an eleventh embodiment of the method according to the present disclosure. Again, it is assumed that the low sodium solution is provided in bags of a known size or volume.

As can be seen from FIG. 5, the method of this embodiment outputs or reveals the number of bags containing low sodium solution that should be used for treating a patient. Depending on the blood sodium concentration (Na+ in [mmol/L]) as one value and the overhydration OH as another value the doctor or the patient may learn from the look-up diagram of FIG. 5 how many bags of low sodium solution or in combination with different glucose concentrations, for example as shown in FIG. 1*a* to 1*d*, should be used in the treatment of the patient. This can be 4 bags in those areas of the diagram shown in FIG. 5 that are marked with 4B, and 2 bags where 2B is stated.

In the example of FIG. 5, no low sodium solution bags are suggested if the patient's sodium concentration in blood is below 136 mmol/l or if the patient is not overhydrated (i.e., the overhydration OH is 0 liter or less (with "less" meaning that the patient is actually underhydrated).

Figure 6:
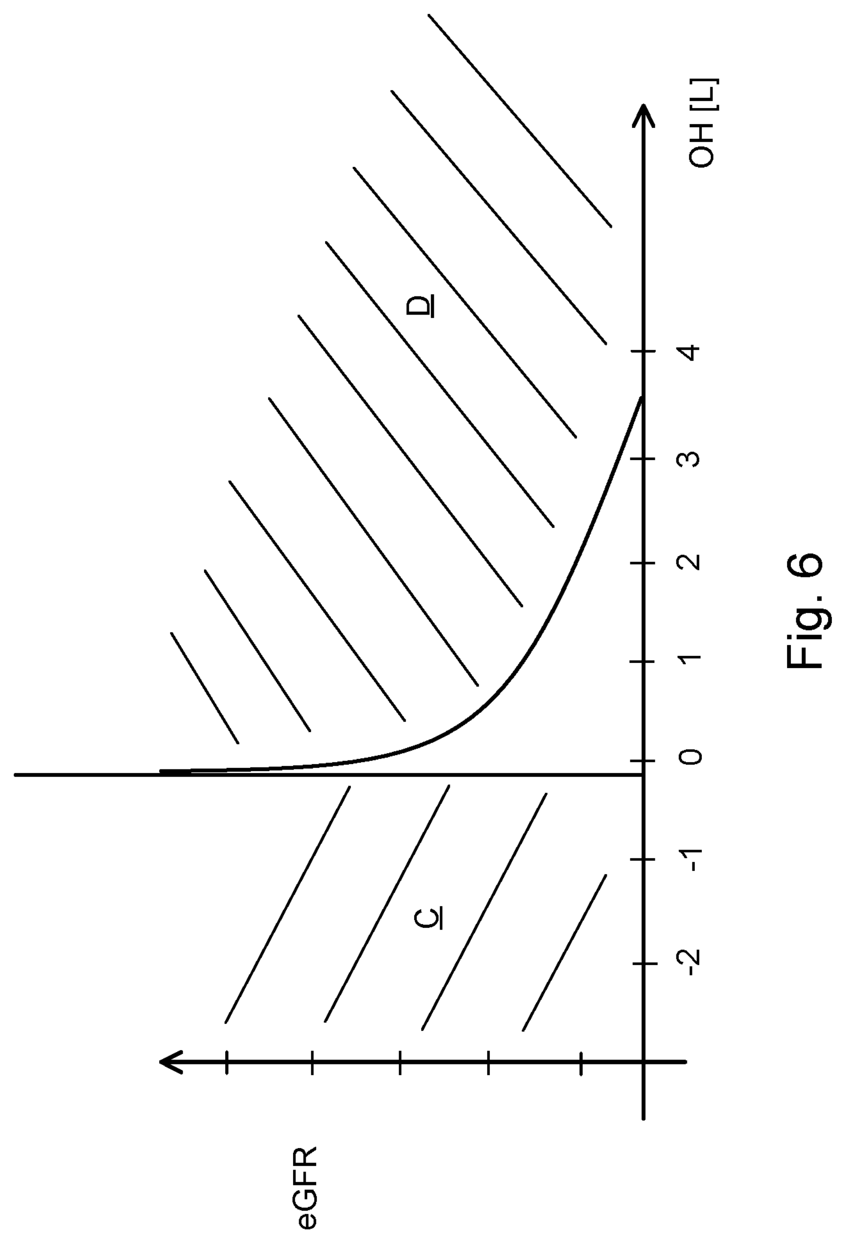
FIG. 6 shows a graphical representation of possible outcomes of the method according to the present disclosure in a twelfth embodiment.

FIG. 6 shows a graphical representation of the outcome of a twelfth embodiment of the method according to the present disclosure.

As can be seen from FIG. 6, after having taken both the overhydration OH values (having the dimension "liter" [L] or OH/ECW (extracellular water) or indexed)) and the estimated glomerular filtration rate (eGFR) or, as one of its alternatives, the residual renal filtration rate (RRF) into account it is determined by the method that patients who do not suffer from overhydration (e.g. having 0 liter fluid excess as in the example of FIG. 6, or being overhydrated by, e.g., at most 1 liter, 2 liters or any other pre-determined value), should not be administered a drug that effects the colloid osmotic pressure such as Maltodextrin or Icodextrin. In this embodiment this applies to patients irrespective of their eGFR value, see shaded area C. As stated before, the vertical line in FIG. 6 separating area C from area D may start in other embodiments at 1 liter OH, 2 liter OH or at yet another OH value.

Also, with increasing overhydration OH and decreasing eGFR values administering drugs such as Maltodextrin or Icodextrin should be considered. The eGFR/OH values combinations of those patients are represented by the shaded area D in FIG. 6.

The graphical representations of FIG. 1 to FIG. 6 may be understood as look-up diagrams, look-up tables, or any other reference materials including maps or the like.

Also, the information shown in FIG. 1 to FIG. 6 may be provided by an output device or unit such as a monitor, a display, a plotter, and the like. In each case, it may be computed by the help of an algorithm.

What has been stated above to reference material and output devices is, of course, not limited to the embodiments of FIG. 1 to FIG. 6. Rather, any outcome gained by the method according to the present disclosure can be the result of using reference material or an algorithm.

Figure 7:
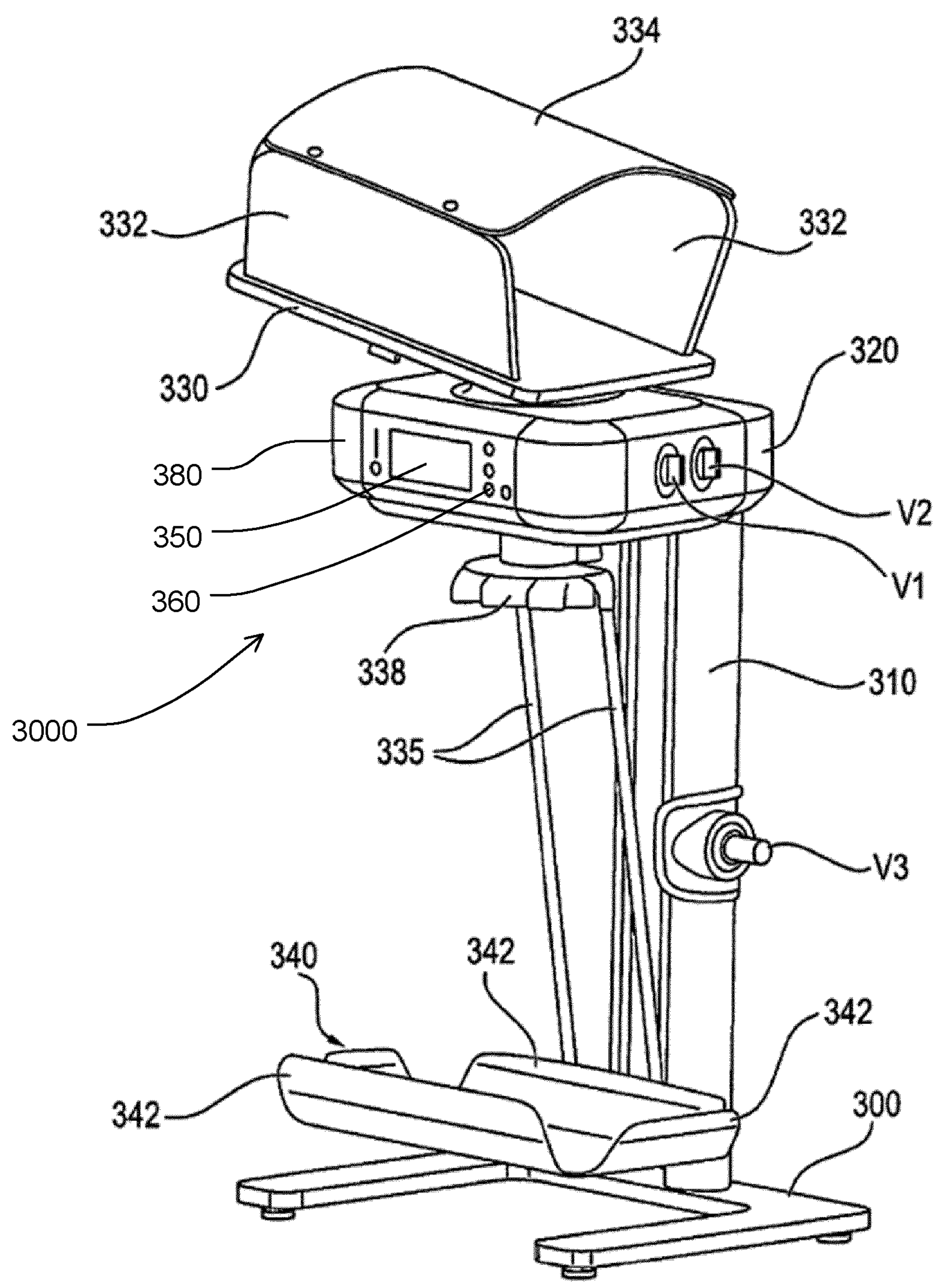
FIG. 7 shows a treatment apparatus according to an exemplary embodiment of the present disclosure in a perspective view.

FIG. 7 shows a gravimetric peritoneal dialysis apparatus 3000 in accordance with the present disclosure in a perspective view. The peritoneal dialysis apparatus 3000 is an exemplary embodiment of a treatment apparatus according to the present disclosure.

The peritoneal dialysis apparatus 3000 comprises an optional pedestal 300, which is optionally U-shaped, from which an apparatus housing support 310 may extend vertically upwardly. The apparatus housing 320 may be located at the upper end of the support 310.

Figure 8:
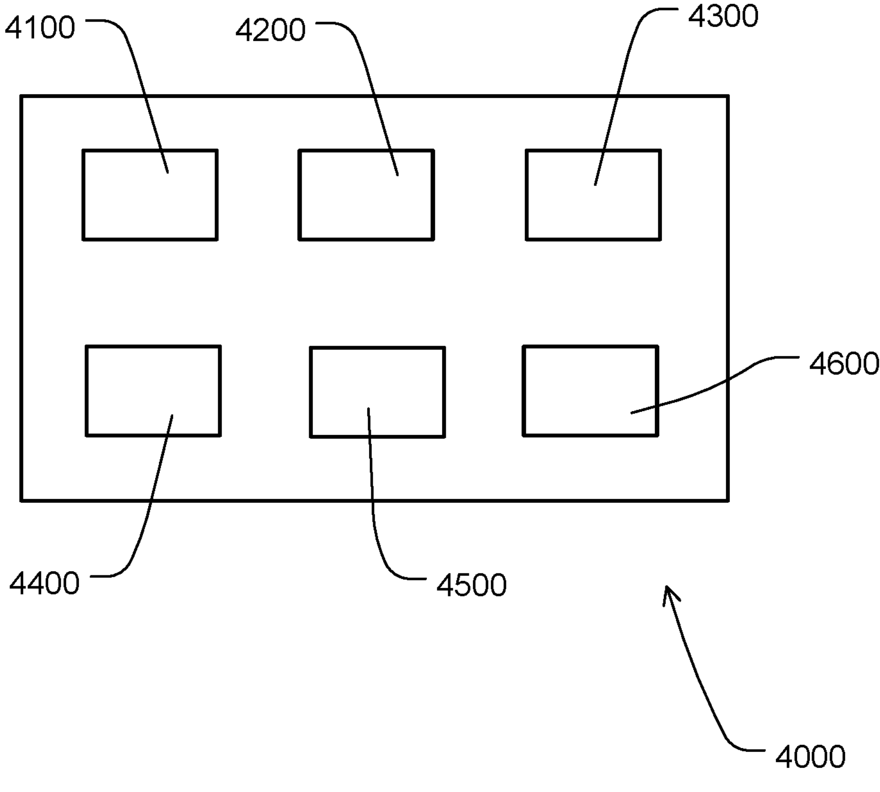
FIG. 8 shows a device according to the present disclosure in an exemplary embodiment.

The electronics required for operating the apparatus, such as control and regulation units, and the operating and/or display units, are located in the apparatus housing 320. They can be integrated into a control or closed-loop control device 380 only shown in FIG. 8. Details are shown in FIG. 8.

An optional heating pan 330 which serves to receive or take solution bags containing fresh dialysis fluid or dialysis solution to be supplied to the patient is arranged above the apparatus housing 320. It may be directly connected thereto.

An optionally provided rod assembly 335 at which an optional weighing pan 340 can be arranged, as in FIG. 7, is located at the bottom at the apparatus housing 320, at an optional weighing cell 338 or at any other suitable position.

The weighing pan 340 serves to receive one or more receiving bags into which the used dialysate coming from the patient flows.

As can be seen from FIG. 7, the weighing pan 340 can be located directly above the floor on which the pedestal 300 of the peritoneal dialysis apparatus stands. It can furthermore be seen from FIG. 7 that the pedestal 300 may have a flat profile so that the weighing pan 340 can be arranged close to the floor. This particular arrangement, however, is not mandatory.

The control of flows to and from the patient may take place via valves, wherein the valve or valves for the fluid connection between the dialysis solution bag or bags, which may be provided in the heating pan 330, and the patient are arranged at the apparatus housing 320, for example.

These valves are denoted with reference numeral V1, V2 in FIG. 7. A drainage valve V3, which may be arranged between the patient and the bag for receiving used dialysate, may be located at the apparatus housing support 310.

As can be seen from FIG. 7, the rod assembly 335 may extend from the rear side of the weighing pan 340 upwards to the lower side of the apparatus housing 320. Thus, the front side of the weighing pan 340 is easily accessible.

The rod assembly 335 is preferably arranged at the optional weighing cell 338 which may be located at or in the apparatus housing 320.

Both the heating pan 330 and the weighing pan 340 have a support surface for supporting the bag or bags. It represents a base. Optional side walls 332 and 342 may extend upwards starting from the base. They are supposed to hold the respective received bags securely in the pan. This may be of particular interest when a plurality of bags is received in the heating pan 330 and in the weighing pan 340 at the same time.

The side walls 332 and 342 can be fastened to the support surface by a plug-in connection or can be pivotable relative to it so that the bags can be placed and removed easily.

The heating pan 330 is optionally provided with an upper cover 334 which may help maintaining the heat, where possible, in the region of the solution bags which are located in the heating pan 330.

Also, as any treatment apparatus according to the present disclosure the peritoneal dialysis apparatus 3000 may comprise an optional display unit 350 and a confirmation unit 360.

The display unit 350, which also may serve as an input device, and/or confirmation unit 360 may be part of the control device 380 indicated to be comprised within the apparatus housing 320.

Figure 7A:
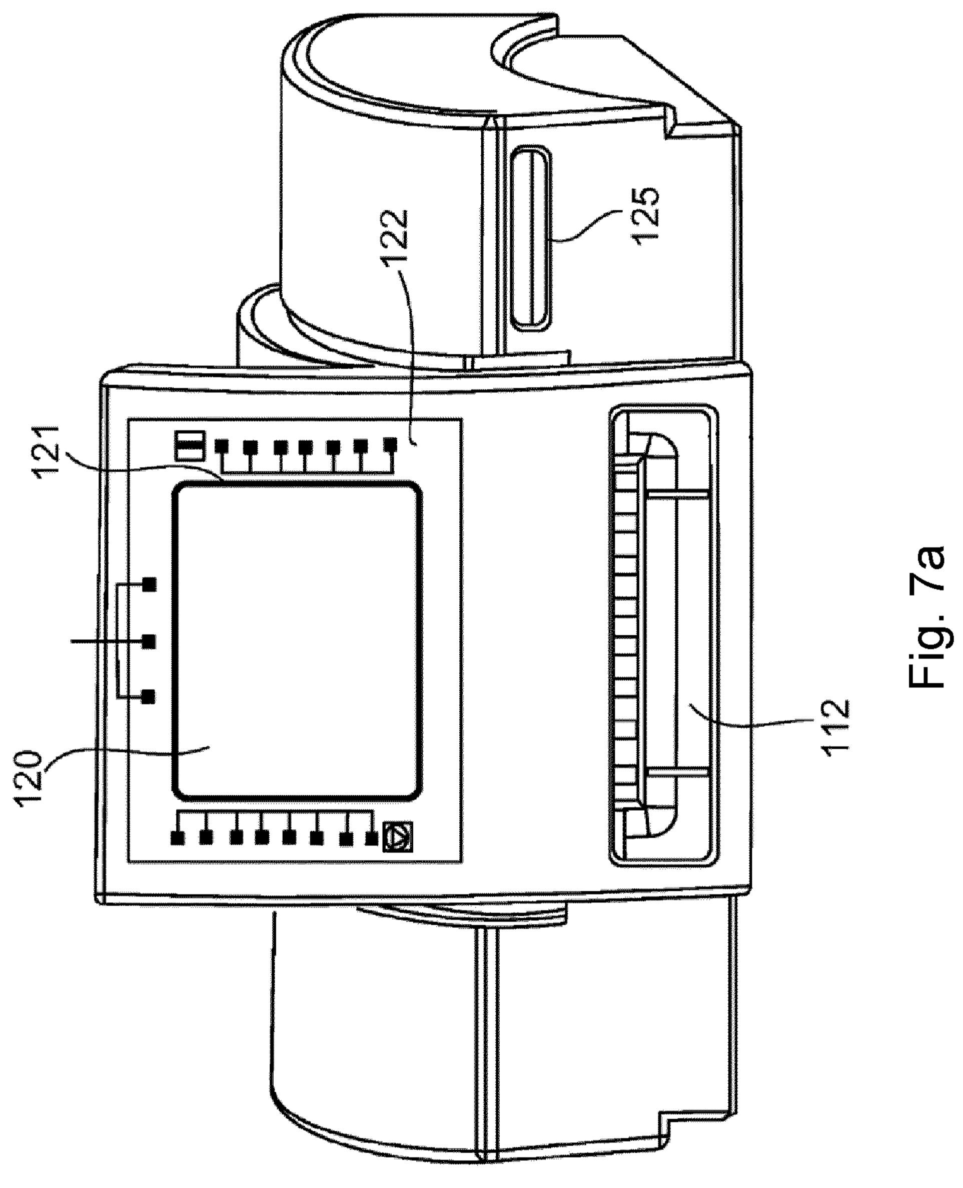
FIG. 7*a* shows a treatment apparatus according to another exemplary embodiment of the present disclosure in a perspective view.

FIG. 7*a* shows a treatment apparatus according to another exemplary embodiment of the present disclosure in a perspective view.

In automatic peritoneal dialysis, a dialysis machine controls and monitors the introduction of the fresh dialysate into the abdominal cavity and the draining of the consumed dialysate (also referred to as spent dialysate). Such a dialysis machine, also called a cycler, usually fills and drains the abdominal cavity several times overnight, while the patient is asleep.

The above-noted dialysis machine comprises a controller that controls a pump, a heater and valves on the basis of the data of sensors. The controller may provide the automatic procedure of the peritoneal dialysis. The controller may include a balance which balances the fluid quantities supplied to and removed from the patient. The balance, if provided, prevents the patient from being given too much fluid or having too much fluid removed.

The dialysis machine shown in FIG. 7*a* may be used with a cassette not shown.

The insertion of the cassette can take place in different ways. For example, in the dialysis machine which is shown in FIG. 7*a*, a drawer can be moved out of the dialysis machine to receive the cassette. The cassette is inserted into this drawer. The cassette is then pushed into the dialysis machine together with the drawer. The pressing of the cassette with the coupling surface which is arranged in the interior of the apparatus is carried out by moving the cassette and the coupling surface mechanically toward one another and then pressing them together pneumatically.

The dialysis machine of FIG. 7*a* optionally has an apparatus for automatic connecting. A connector receiver 112 is provided for this purpose into which the connectors of the dialysate bag are inserted. The connector receiver 112 then moves into the apparatus where a barcode reader is provided which reads the barcodes applied to the connectors. The apparatus can thus check whether the correct bags were inserted. If the correct bags are recognized, the connector receiver 112 moves in completely and so connects the connectors of the bag to the connections of the cassette made as connectors.

In the dialysis machines of FIG. 7*a*, an optional touch screen 120 is provided which allows an interactive menu navigation. Optional display elements 121 and 122 are also provided which show states of the dialysis machine in compact form. The dialysis machine preferably also has a card reader 125 via which a patient card can be read. Data on the treatment of the respective patient can be stored on the patient card. The treatment procedure for the respective patient can hereby be individually fixed.

A dialysis machine as described before (or similar to that) is described in WO 12/076179, the respective disclosure of which is incorporated herewith by way of reference.

FIG. 8 shows a device 4000 according to the present disclosure in one embodiment.

The device 4000 may be a stand-alone device. Alternatively, it is part of another device or apparatus such as the treatment apparatus according to the present disclosure. It can, by way of example, be part of the peritoneal dialysis apparatus 3000 of FIG. 7 or of an APD Cycler shown in FIG. 7*a*. For example, it may be part of the control device 380 and/or covered by the apparatus housing 320 shown in FIG. 7, by the housing shown in FIG. 7*a* or by the housing of the treatment apparatus in any other embodiment according to the present disclosure.

The device 4000 may comprise a computing unit 4100, a storage unit 4200, a transfer unit 4300 for sending the suggested treatment modality to another entity such as a display unit 4400 and a confirmation unit 4500. It may also have an inhibiting unit 4600. They all can be in signal communication with each other. However, none of these units 4100 to 4600 are mandatory.

The computing unit 4100 may be configured to carry out the method according to the present disclosure, e.g., the step of determining, calculating, looking-up and/or setting the at least one treatment modality.

The storage unit 4200, if provided, may be where the result of the present disclosure, i.e., is stored for future use or future treatments. Also, the treatment modality originating from running the method may be stored here for documentation reasons.

The transfer unit 4300, if provided, may be configured to transfer information concerning the treatment modality to the treatment apparatus, to an external display unit, a printer, a monitor, a hand-held item such as a smart phone, a digital personal assistant, or the like or to a doctor's working place or desk or anywhere else where this information may be of interest.

The display unit 4400 may be embodied like the display unit 350 shown in FIG. 7. In fact, both display units might be one and the same element.

The confirmation unit 4500 may be embodied like the confirmation unit 360 shown in FIG. 7. In fact, both confirmation units might be one and the same element.

The inhibiting unit 4600 may be provided and configured for not allowing, or inhibiting, at least one pre-determined action in case the user has not yet acknowledged the treatment modality suggested by the method. The inhibition may include closing a valve, e.g., one or more of valves V1, V2 or V3, stopping a pump, blocking a start button, or the like.

In some embodiments, the device 4000 itself is a hand-held gadget, a smart phone or a digital personal assistant.

Although not shown in the figures, any arbitrary combination of one or more of the units 4100 to 4600 can also be part of any embodiment of the treatment apparatus according to the present disclosure.

REFERENCE NUMERALS

A shaded area
B shaded area
C shaded area
D shaded area
BP blood pressure
OH overhydration
eGFR estimated glomerular filtration rate
RRF residual renal filtration rate
0B no low sodium bags
2B two low sodium bags
4B four low sodium bags
112 connector receiver
120 touch screen
121 display element
122 display element
125 card reader
3000 peritoneal dialysis apparatus
300 pedestal
310 apparatus housing support
320 apparatus housing
330 heating pan
332 side wall
334 upper cover
335 rod assembly
338 weighing cell
340 weighing pan
342 side wall
350 display unit
360 confirmation unit
380 control or closed-loop control device
V1, V2, V3 valves
4000 device
4100 computing unit
4200 storage unit
4300 transfer unit
4400 display unit
4500 confirmation unit
4600 inhibiting unit

The invention claimed is:

1. A computer-implemented method for determining at least one treatment modality of a dialysis treatment of a specific patient using a dialysis liquid, the method comprising:

receiving at least one value out of a group of values, the group of values consisting of: a first value reflecting an over hydration (OH) of the patient, a second value reflecting a salinity or osmolarity of the patient, a third value reflecting a blood pressure of the patient, a fourth value reflecting a renal function of the patient, a fifth value reflecting a heart issue of the patient, a sixth value reflecting hypotension of the patient, a seventh value reflecting vessel conditions, and an eighth value reflecting a total protein content of the patient;

determining the at least one treatment modality for an upcoming treatment of the specific patient using the at least one value out of the group of values and using reference material, wherein determining the at least one treatment modality comprises determining a number of bags to be used in the upcoming treatment of the specific patient, wherein each bag of the number of bags contains a dialysis liquid with sodium concentrations lower than 135 mmol/liter, wherein the reference material comprises stored information from previous treatments of the patient and at least one threshold value based at least in part on the stored information from the previous treatments, and wherein determining the at least one treatment modality comprises comparing the at least one value out of the group of values to the at least one threshold value of the reference material;

outputting a result of the determination on a display; and upon the determining of the at least one treatment modality, automatically controlling a treatment apparatus to automatically initiate the upcoming treatment on the specific patient, wherein the upcoming treatment uses the number of bags.

2. The method according to claim 1, wherein determining the at least one treatment modality comprises determining one or more bags selected from a multitude of bags with different salinities, and/or one or more bags containing specific concentrations of an osmotic agent.

3. The method according to claim 1, wherein determining the at least one treatment modality is or comprises determining a salinity or a sodium content or concentration of the dialysis liquid to be used.

4. The method according to claim 1, further comprising setting the use of glucose.

5. The method according to claim 1, further comprising saving or storing the determined or set at least one treatment modality in a storage unit of a device or in a control device of a treatment apparatus.

6. The method according to claim 1, further comprising providing an alert that the at least one value indicates danger to the patient.

7. The method according to claim 1, wherein the at least one value is directly measured.

8. The method according to claim 1, wherein the at least one value is derived indirectly from other values.

9. The method according to claim 1, wherein the dialysis liquid is a peritoneal dialysis solution.

10. A device configured to carry out the method according to claim 1.

11. A treatment apparatus having treatment devices for treating a patient using a dialysis liquid, the treatment apparatus having or being connected to a control or closed-loop control device, wherein the control or closed-loop control device is configured to execute the method according to claim 1.

12. The treatment apparatus according to claim 11, wherein the control or closed-loop control device is configured to execute a treatment of the patient in interaction with the treatment devices of the treatment apparatus based on the determined or set at least one treatment modality.

13. The treatment apparatus according to claim 11, comprising a display unit, wherein the control or closed-loop control device is configured to display the treatment modality using the display unit.

14. The treatment apparatus according to claim 13, comprising a confirmation unit by which the displayed treatment modality is to be confirmed, wherein the control or closed-loop control device is configured to not allow a treatment unless or until a user confirms or has confirmed that the user has noted the treatment modality displayed.

15. The treatment apparatus according to claim 11, wherein the control or closed-loop control device is configured to not allow a treatment unless or until a user enters the information that the determined or set treatment modality has been provided.

16. The treatment apparatus according to claim 11, wherein the treatment apparatus is one of: a peritoneal dialysis machine, an automatic peritoneal dialysis cycler a continuous ambulatory peritoneal dialysis system, a haemodialysis machine, a haemofiltration machine, or a haemodiafiltration machine.

17. The treatment apparatus according to claim 16, wherein the treatment apparatus is configured to consult an external database periodically to check available drugs and/or drug dosages and/or recommendations of current guidelines.

18. A method of treating a patient using a treatment apparatus and a dialysis liquid, wherein the treatment modality is calculated or set based on the method according to claim 1.

19. A digital storage unit with electronically readable control signals which are able to interact with a programmable computer system such that the method according to the claim 1 will be executed.

20. A computer program product for executing the method according to claim 1 when executing the computer program product on a computer.

21. A computer program with a program code for the execution of the method according to claim 1 when executing the program on a computer.

22. The method according to claim 1, wherein the reference material is in the form of an algorithm.

23. The method according to claim 1, wherein the stored information is in the form of a reference table.

* * * * *